United States Patent [19]

Gold et al.

[11] 4,183,923

[45] Jan. 15, 1980

[54] ANTIPSORIATIC COMPOSITIONS

[75] Inventors: Elijah H. Gold, West Orange; Daniel M. Solomon, Edison, both of N.J.

[73] Assignee: Schering Corporation, Kenilworth, N.J.

[21] Appl. No.: 849,362

[22] Filed: Nov. 7, 1977

[51] Int. Cl.$^2$ ............................................. A61K 31/58
[52] U.S. Cl. ............................... 424/241; 260/239.5; 260/239 A; 424/244
[58] Field of Search ............................... 424/241, 244; 260/239.5

[56] References Cited

FOREIGN PATENT DOCUMENTS 1264253  2/1972  United Kingdom .

*Primary Examiner*—Elbert L. Roberts
*Attorney, Agent, or Firm*—Barbara L. Cowley Renda; Mary S. King; Bruce M. Eisen

[57] ABSTRACT

Disclosed herein are compositions containing 1-substituted-3-alkanesulfonyloxyazetidines, useful in the treatment of psoriasis.

18 Claims, No Drawings

ANTIPSORIATIC COMPOSITIONS

BACKGROUND OF THE INVENTION

Psoriasis is a common chronic, recurrent, inflammatory disease of the skin characterized by rapid multiplication and turnover of the epithelial cells with a consequent thickening of the epidermis, as well as an accumulation of incompletely maturized cells in the stratum corneum resulting in dry scaling patches. Its etiology is unknown and presently available therapeutic agents are generally not satisfactory. The disease is estimated to affect as much as 1-2% of the population and, while not fatal, it is socially, psychologically, physically and economically crippling to its victims.

SUMMARY OF THE INVENTION

The present invention relates to compositions containing 1-substituted-3-alkanesulfonyloxyazetidines which are useful in the treatment of psoriasis. More particularly, this invention relates to compositions containing an antipsoriatic amount of a compound of the formula:

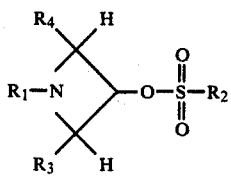
(I)

wherein $R_1$ is selected from the group consisting of hydrogen, alkyl groups containing from 3 to 18 carbon atoms, cycloalkyl groups containing from 5 to 15 carbon atoms, 1-adamantyl, 2-adamantyl, benzhydryl, benzyl, dihydroxybenzyl, dialkoxybenzyl, dibenzyloxybenzyl, 3-(5α-cholestane) and 3-(5α-androstan-17-one) groups; $R_2$ is selected from the group consisting of alkyl groups containing 1 to 18 carbon atoms, benzyl and tolyl; and $R_3$ and $R_4$ are independently hydrogen or alkyl of 1-4 carbon atoms.

In addition to the free bases of formula I, the pharmaceutically acceptable acid addition salts are contemplated within the scope of this invention. Such acid addition salts can be derived from a variety of inorganic and organic acids such as sulfuric, phosphoric, methanesulfonic, sulfamic, citric, lactic, pyruvic, oxalic, maleic, stearic, succinic, tartaric, fumaric, cinnamic, aspartic, acetic, benzoic, salicylic, gluconic, ascorbic and related acids.

The alkyl groups referred to above contain either 1-4, 3-18 or 1-18 carbon atoms and include both straight and branched-chain radicals. Such groups are exemplified by methyl, ethyl, n-propyl, isopropyl, butyl, isobutyl, tert-butyl, pentyl, hexyl, isohexyl, heptyl, 3,7-dimethyl-1-octyl, 8-pentadecyl, 1-hexadecyl, 1-octadecyl, and the like.

The cycloalkyl groups referred to above contain from 5-15 carbon atoms and are exemplified by groups such as cyclopentyl, cyclohexyl, cycloheptyl, cyclopentadecyl and the like.

The lower alkoxy groups referred to above contain 1-4 carbon atoms and are exemplified by methoxy, ethoxy, propoxy, butoxy and the corresponding branched-chain isomers.

Where the possibility for position variation exists in the above substituted phenyl rings, this invention is intended to encompass such variation. Thus, tolyl includes o-tolyl, m-tolyl, and p-tolyl and dihydroxybenzyl, dialkoxybenzyl and dibenzyloxybenzyl include 2,3-, 2,4-, 2,5-, 2,6-, 3,4- and 3,5-disubstitutions.

Preferred compounds for use in the compositions of the present invention are those compounds wherein $R_2$ is a methyl group. Particularly preferred are those compounds wherein $R_2$ is a methyl group and $R_1$ is an isopropyl or 3α-(5α-cholestane) group. A highly preferred compound is 1-isopropyl-3-methanesulfonyloxyazetidine hemimaleate.

DETAILED DESCRIPTION OF THE INVENTION

Certain of the compounds useful in the compositions of the present invention are known in the chemical arts. For instance, Belgian Pat. No. 745,173 and British Pat. No. 1,264,253 disclose the compounds of formula I wherein $R_1$ is a hydrocarbon radical having 4-13 carbon atoms, and $R_2$ is an alkyl or aryl group. Similarly, U.S. Pat. No. 3,929,765 generically discloses the compounds where $R_1$ is an "aliphatic, alicyclic or aromatic hydrocarbon residue." Japanese Pat. No. 7,213,500 also discloses compounds wherein $R_1$ is a hydrocarbon radical of 1-15 carbon atoms and $R_2$ is a hydrocarbon group.

Certain of the compounds useful in the present invention are novel compounds, heretofore unknown in the chemical art. For example, the compounds of the formula:

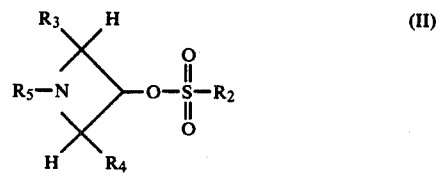
(II)

wherein $R_2$, $R_3$ and $R_4$ are as hereinbefore defined and $R_5$ is a 3-(5α-cholestane) or 3-(5α-androstan-17-one) group, are novel. The compounds of formula II contain the possibility of an α- or β-linkage at the $R_5$-N bond. As such, our invention encompasses both the α- and β-stereochemical forms and mixtures thereof.

The compounds useful in the compositions of the present invention may be prepared by reaction of the appropriate 1-substituted-3-hydroxyazetidine of the formula:

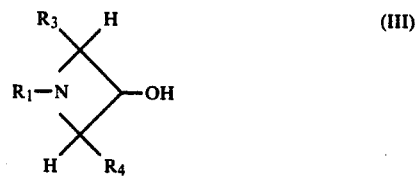
(III)

wherein $R_1$, $R_3$ and $R_4$ are as hereinbefore defined with the appropriate alkanesulfonyl chloride of the formula:

(IV)

wherein R₂ is as hereinbefore defined in the presence of a suitable acid acceptor. This reaction is most preferably conducted in an inert organic solvent such as benzene, toluene, ethyl ether or tetrahydrofuran. The acid acceptor may be an organic base such as pyridine or triethylamine, or an inorganic base such as potassium or lithium hydride.

This method is preferred for the preparation of:

1-benzyl-3-methanesulfonyloxyazetidine,
1-(2,3-diethoxybenzyl)-3-methanesulfonyloxyazetidine,
1-(3,4-dimethoxybenzyl)-3-methanesulfonyloxyazetidine,
1-(3,4-dibenzyloxybenzyl)-3-methanesulfonyloxyazetidine,
1-(3,4-dihydroxybenzyl)-3-methanesulfonyloxyazetidine,
1-isopropyl-3-(p-toluenesulfonyloxy)azetidine,
1-isopropyl-3-(α-toluenesulfonyloxy)azetidine,
1-t-butyl-3-(p-toluenesulfonyloxy)azetidine,
1-isopropyl-3-methanesulfonyloxyazetidine,
1-(2-butyl)-3-methanesulfonyloxyazetidine,
1-t-butyl-3-methanesulfonyloxyazetidine,
1-isopropyl-3-isopropanemethanesulfonyloxyazetidine,
1-isopropyl-3-ethanesulfonyloxyazetidine,
1-isopropyl-3-(1-hexadecanesulfonyloxy)azetidine,
1-(8-pentadecyl)-3-methanesulfonyloxyazetidine,
1-(2-pentyl)-3-methanesulfonyloxyazetidine,
1-cyclohexyl-3-methanesulfonyloxyazetidine,
1-cyclopentadecyl-3-methanesulfonyloxyazetidine,
1-(1-adamantyl)-3-methanesulfonyloxyazetidine,
1-(2-adamantyl)-3-methanesulfonyloxyazetidine,
1-(3-hexyl)-3-(p-toluenesulfonyloxy)azetidine,
1-isopropyl-2,4-dimethyl-3-methanesulfonyloxyazetidine,
1-isopropyl-2-methyl-3-methanesulfonyloxyazetidine,
1,2-diisopropyl-3-methanesulfonyloxyazetidine,
1-benzhydryl-3-methanesulfonyloxyazetidine, and
1-benzhydryl-3-hexanesulfonyloxyazetidine, The compounds of the present invention wherein R₁ is an alkyl, 3-(5α-cholestane) or a 3-(5α-androstan-17-one) group may alternatively be prepared by reaction of a compound of the formula:

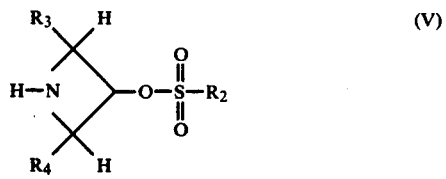
(V)

wherein R₂, R₃ and R₄ are as hereinbefore defined, with the appropriate aldehyde, ketone, 5α-cholestane-3-one or 5α-androstane-3,17-dione in the presence of a reducing agent. The reducing agent may be hydrogen and a catalyst, i.e., palladium, palladium-on-carbon or palladium hydroxide-on-carbon; or other such reducing agents known in the chemical arts, e.g., sodium cyanoborohydride. This reaction is preferably conducted in an organic solvent such as methanol, ethyl ether or tetrahydrofuran. This is a convenient route to compounds such as:

3α-(3-methanesulfonyloxy-1-azetidinyl)-5α-cholestane,
3α-(3-methanesulfonyloxy-1-azetidinyl)-5α-androstan-17-one,
3β-(3-methanesulfonyloxy-1-azetidinyl)-5α-androstan-17-one,
3β-(3-methanesulfonyloxy-1-azetidinyl)-5α-cholestane,
3β-(3-p-toluenesulfonyloxy-1-azetidinyl)-5α-cholestane,
3-[3-(1-hexanesulfonyloxy)-1-azetidinyl]-5α-cholestane,
3-[3-(1-octanesulfonyloxy)-1-azetidinyl]-5α-cholestane,
3α-[3-(1-hexadecanesulfonyloxy)-1-azetidinyl]-5α-cholestane,
1-isopropyl-3-methanesulfonyloxyazetidine,
1-isopropyl-3-hexadecanesulfonyloxyazetidine, and
1-(3,7-dimethyl-1-octyl)-3-methanesulfonyloxyazetidine.

Alternatively, the

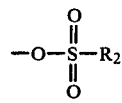

group of formula V may be a hydroxy group. When this is the case, the reaction affords the starting material of formula III wherein R₁ is a 5α-cholestane or 5α-androstan-17-one group.

A useful synthetic procedure for production of certain of the intermediates of formula III involves the reaction of 3-hydroxyazetidine (or a salt thereof) with an acid chloride of the formula:

(VI)

wherein R₆ is an alkyl group containing from 2 to 17 carbon atoms in the presence of an acid acceptor. A particularly useful acid acceptor is pyridine due to its double role as a solvent and an acid acceptor, but other organic and inorganic bases may also be used. The resultant compound of the formula

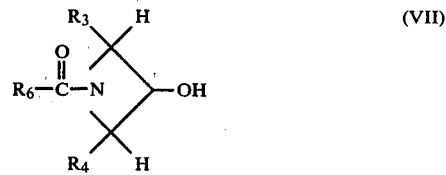
(VII)

is then subjected to reduction with a suitable reducing agent to afford the intermediate of formula III wherein R₁ is an alkyl group containing 3 to 18 carbon atoms. A particularly suitable reducing agent is diborane in tetrahydrofuran.

Synthetic sequences utilizing intermediates of the type of formulae VI and VII are particularly useful for the preparation of:

1-octadecyl-3-(1-hexadecanesulfonyloxy)azetidine,
1-octadecyl-3-p-toluenesulfonyloxyazetidine,
1-hexadecyl-3-methanesulfonyloxyazetidine,
1-octadecyl-3-methanesulfonyloxyazetidine,
1-tetradecyl-3-methanesulfonyloxyazetidine,
1-octadecyl-3-(1-hexanesulfonyloxy)azetidine, and
1-hexadecyl-3-(1-octanesulfonyloxy)azetidine.

The free base form of the compounds of formula I may be conveniently converted to the corresponding acid addition salt by conducting a solution of the free base with the appropriate acid. Particularly preferred salts are the acid addition salts formed with maleic acid, e.g., maleates and hemi-maleates.

The antipsoriatic activity of the compounds of this invention can be determined by measurement of the effect of the test compound in a four day histologic screen for antiepidermal activity and in an in vitro protein synthesis assay. Both assays employ the guinea pig ear epidermis in which a psoriaform lesion has been produced by stripping and retinoic acid pretreatment. In these assays, representative compounds of this invention, i.e., 3-methanesulfonyloxyazetidine methane sulfonate, 1-(1-adamantyl)-3-methanesulfonyloxyazetidine hemimaleate, 1-isopropyl-3-methanesulfonyloxyazetidine hemimaleate and 3α-(3-methanesulfonyloxyazetidinyl)-5α-cholestane hemimaleate are active in reducing or eliminating psoriatic symptoms at a dose of 4 mg/application or less.

The compositions of the present invention comprise a compound of formula I in an antipsoriatic amount together with a suitable pharmaceutical carrier. An antipsoriatic amount is defined as the amount of compound necessary to cause remission of the psoriatic symptoms, i.e., the psoriatic lesions. In the usual course of therapy, the active compound is incorporated into an acceptable vehicle to form a composition for topical administration to the affected area, or into a form suitable for oral administration, such as tablets, capsules or pills.

Compositions for topical application may be exemplified by ointments, creams, lotions, solutions, suspensions, aerosols, gels, shampoos, soaps or dusting powders. Such compositions will normally be based upon standard carriers such as pharmaceutically acceptable vegetable oils and gelatin, gums and petrolatum. Other ingredients to the compositions of the present invention may be preservatives, coloring, flavoring, sweetening, thickening, suspending, dispersing, emulsifying, swelling, stabilizing, and buffering agents as required by the specific formulation. Such compositions are envisioned to contain the active ingredient in a 0.05-5% by weight amount.

Compositions for oral administration, other than the dosage units mentioned above may be exemplified by lozenges, dragees, powders, granulates, solutions, suspensions, or elixirs.

The required daily dosage may be administered in single or divided doses. The exact dose to be administered will, of course, be dependent upon the particular compound employed, the age and weight of the subject and the patient's individual response. Based on animal testing and comparisons with known active agents, typical doses of the compounds of formula I for topical administration for the treatment of psoriasis, mycosis fungoides and vitiligo are contemplated to be in the range of 0.01-5 mg/kg daily. This daily amount may be administered in single or divided doses.

The following examples describe in detail compounds and compositions illustrative of the present invention and methods which have been devised for their preparation. It will be apparent to those skilled in the art that many modifications, both of materials and methods, may be practiced without departing from the purpose and intent of this disclosure.

EXAMPLE 1

1-Isopropyl-3-Methanesulfonyloxyazetidine Hemimaleate

Heat a mixture of 1.0 mole 1-chloro-2,3-epoxypropane and 0.5 mole diphenylmethylamine in N,N-dimethylformamide at about 95° C. for 48 hours. Cool the solution with agitation to less than 10° C. and slowly add 6 N hydrochloric acid at such a rate as to maintain the temperature below 25° C. Filter the resultant precipitate, wash it several times with diethyl ether and air dry.

Dissolve the hydrochloride salt in a 1:1 mixture of sodium hydroxide and diethyl ether. Separate the ether layer and extract the water layer several times with diethyl ether. Dry the combined ether extract over anhydrous sodium sulfate and remove the ether by distillation to afford 1-benzhydryl-3-hydroxyazetidine.

Slowly add 1.0 mole of methanesulfonyl chloride to an agitating solution of 1.0 mole 1-benzhydryl-3-hydroxyazetidine and triethylamine in benzene or toluene maintained at 10° to 15° C. Agitate the reaction mixture at 15° to 18° C. for half an hour, then at 20°–23° C. for another half hour. Add diethyl ether and agitate for 10 minutes longer. Remove the triethylamine hydrochloride precipitate by filtration and add the filtrate to a solution of 1.0 mole maleic acid in diethyl ether and stir for about one hour. Isolate the product 1-benzhydryl-3-methanesulfonyloxyazetidine as the hemimaleate salt (1:1) by filtration.

Prepare 1-benzhydryl-3-methanesulfonyloxyazetidine by treating a suspension of the maleate salt (1.0 mole in water with 1.1 M sodium bicarbonate and extracting with 4:1 diethyl ether:methylene chloride followed by 3:1 diethyl ether:methylene chloride. Wash the combined extracts several times with 1.1 M sodium bicarbonate, then with saturated aqueous sodium chloride. Dry the extracts over anhydrous sodium sulfate and remove the solvents by distillation to yield 1-benzhydryl-3-methanesulfonyloxyazetidine.

Hydrogenate a mixture of 1.0 mole 1-benzhydryl-3-methanesulfonyloxyazetidine, 1.0 mole methanesulfonic acid and 20% palladium hydroxide-on-carbon in ethyl alcohol at ca. 60 psi until the reaction is complete as shown by absence of the Compound IV using thin layer chromatography. (Silica gel GF plates are developed in chloroform:ethyl acetate (9:1) and visualized using iodine). Add additional 20% palladium hydroxide-on-carbon and acetone and continue the hydrogenation at ca. 60 psi for 5 days. Remove the catalyst by filtration and wash with ethanol. Remove the ethanol from the combined filtrates and washes by distillation at about 40° C. under reduced pressure and wash the residue with diethyl ether and air-dry to afford 1-isopropyl-3-methanesulfonyloxyazetidine methanesulfonate.

Add 1.0 mole of 1-isopropyl-3-methanesulfonyloxyazetidine methanesulfonate and chloroform to aqueous 1.1 M sodium bicarbonate with agitation. Saturate the aqueous phase with sodium chloride, filter and wash the solid with chloroform. Separate the phases of the combined filtrate and washes and extract the aqueous layer several times with chloroform. Dry the combined extract over sodium sulfate and filter. Add the filtrate to a solution of 1.0 mole of maleic acid in diethyl ether and warm the mixture to about 30° C. Isolate the product, 1-isopropyl-3-methanesulfonyloxyazetidine hemimaleate, by filtration and air-dry. This salt has the ratio of 1 mole 1-isopropyl-3-methanesulfonyloxyazetidine to 1 mole of maleic acid and melts within the range 115°–121° C.

EXAMPLE 2

3α-(3-Methanesulfonyloxy-1-Azetidinyl)-5α-Cholestane

Hydrogenate in a Parr Shaker at 50–60 psi and room temperature a mixture of 8.14 g 1-benzhydryl-3-hydroxyazetidine, 2.04 g acetic acid, and 0.5 g 20% Pd(OH)$_2$/C in 120 ml methanol until the starting azetidinol is no longer detectable by TLC (silica, EtOAc). Add 13.17 g of 5α-cholestan-3-one, 0.3 g 20% Pd(OH)$_2$/C and 90 ml methanol and continue hydrogenation at 50–60 psi and room temperature until TLC (silica, CHCl$_3$) shows no more ketone. Filter catalyst and remove solvent from filtrate in vacuo. Dissolve the resultant residue in 200 ml benzene and treat with 1.2 g liquid ammonia. Filter and remove solvent from the filtrate in vacuo to obtain a mixture of 3α- and 3β-(3-hydroxy-1-azetidinyl)-5α-cholestane.

To a solution of 13.1 g of a mixture of the above 3α- and 3β-epimers and 2.17 g of triethylamine in 210 ml of dry benzene at 5° C. add dropwise a solution of 2.46 g methanesulfonyl chloride in 2 ml dry benzene. Stir the reaction mixture for 1.5 hour at 5° C., then another 1½–2 hours at room temperature. Add 500 ml of ethyl ether and filter solids. Add the filtrate rapidly to a stirred solution of 2.5 g maleic acid in 150 ml of ethyl ether. Filter and wash the resultant precipitate with ethyl ether to obtain the hemimaleate salt of the title product. Dissolve the salt in 100 ml of chloroform and stir with 25 ml 1.1 M aqueous sodium bicarbonate. Separate the organic phase, dry over anhydrous sodium sulfate, and stir solvent in vacuo to obtain the title product, m.p. 136.0°–136.5° C., $[\alpha]_D^{26} = +22.3°$ (CHCl$_3$, 0.8%).

EXAMPLE 3

3β-(3-Methanesulfonyloxy-1-Azetidinyl)-5α-Cholestane

To a stirred suspension of 3.50 g of the mesylate salt of 3-methanesulfonyloxyazetidine (m.p. 111.5°–113° C. dec.) and 5.46 g of 5α-cholestan-3-one in 100 ml of anhydrous methanol maintained at room temperature under a nitrogen atmosphere add 1.74 g sodium cyanoborohydride portionwise over a 20 minute period. Stir for 30 minutes at room temperature, pour into 600 ml water, add to the mixture 100 ml 1.1 M aqueous sodium bicarbonate and extract three times with ethyl ether. Combine the ether extracts, dry over 3 A molecular sieves and remove solvent in vacuo to give a mixture of α- and β-mesylates. Chromatography of this mixture on 150 g Stahl-type silica using ethyl acetate affords the pure title product (slower-moving component), m.p., 135.5° C. dec., $[\alpha]_D^{26} = +12.1°$ (CHCl$_3$, 0.4%).

EXAMPLE 4

3-(3-p-Toluenesulfonyloxy-1-Azetidinyl)-5α-Cholestane

To a nitrogen blanketed, ice-cooled, stirred suspension of 1.08 g of 35% potassium hydride in mineral oil in 58 ml dry tetrahydrofuran and 2–3 ml triglyme add 3.49 g 3-(3-hydroxy-1-azetidinyl)-5α-cholestane (a mixture of the 3α- and 3β-epimers). Continue stirring the mixture for 5 days at room temperature, adding an additional 80 ml dry tetrahydrofuran after the first 24 hours. After 5 days add a solution of 1.52 g of p-toluenesulfonyl chloride in 10 ml tetrahydrofuran and stir one hour. Destroy the excess potassium hydride by the cautious addition of approximately 70 ml of water-saturated ethyl ether; then, add 350 ml water and saturate with sodium chloride. Extract once with 300 ml ethyl ether and then twice with 150 ml portions of ethyl ether. Combine the etheral extracts, dry over anhydrous sodium sulfate, and acidify the solution with a solution of 0.93 g maleic acid in 50 ml ethyl ether. Filter the crude maleate salt and triturate with 150 ml hexane. Dissolve the triturated material in 20 ml methylene chloride and treat the solution with decolourizing carbon. Filter the carbon and dilute the filtrate with 250 ml isopropyl ether. Concentrate the solution in vacuo until a precipitate begins to form. Filter the precipitate to obtain the maleate salt of the title compound, m.p. 105°–109° C. dec. (a mixtuer of 3α- and 3β- epimers).

EXAMPLE 5

3α-(3-Hexadecanesulfonyloxyl-1-Azetidinyl)-5α-Cholestane

To a stirred suspension of 1.5 g 3α-(3-hydroxy-1-azetidinyl)-5α-cholestane (prepared as described in Example 1 and purified by column chromatography, m.p. 191.5°–195.5° C.) and 0.34 g triethylamine in 33 ml dry benzene, add a solution of 0.78 g 98% hexadecanesulfonyl chloride in 7 ml dry benzene. Stir the resultant cloudy solution at room temperature for 20 days. Concentrate the reaction mixture in vacuo to about one-third the original volume and filter the resultant precipitate. Remove the solvent in vacuo from the filtrate. Dissolve the resultant residue in 80 ml ethyl ether and filter through a column of 45–50 g silica gel eluting with additional ethyl ether as needed to afford the title compound, m.p. 64.5°–68.0° C.

EXAMPLE 6

3β-(3-Methanesulfonyloxy-1-Azetidinyl)-5α-Androstan-17-One and
3α-(3-Methanesulfonyloxy-1-Azetidinyl)-5α-Androstan-17-One Hydrogenate at 60 psi and room temperature a mixture of 4.33 g 5α-androstane-3, 17-dione, 8.15 g of the mesylate salt of 3-methanesulfonyloxyazetidine, and 0.5 g of 20% palladium hydroxide-on-carbon in 400 ml methanol until TLC (silica, 1:9 ethyl acetate-chloroform) shows no remaining dione. Filter out catalyst and remove solvent from the filtrate in vacuo. Triturate the residue with 200 ml ethyl ether, decant, and stir the residue with a solution of 40 ml 1.1 M aqueous sodium bicarbonate in 325 ml water. Extract three times with 200 ml portions of methylene chloride, combine the extracts and dry over anhydrous sodium sulfate. Removal of the solvent in vacuo affords a mixture, which is separated by chromatography on 120 g Stahl-type silica using ethyl acetate as the elution solvent to afford the pure title compounds. The 3α-epimer (faster-moving component) melts at 179.5°–181° C. dec. as the free base, and 121°–122.5° C. dec. as the hemimaleate salt. The 3β-epimer (slower moving component) melts at 150.5°–151° C. dec. as the hemimaleate salt.

EXAMPLE 7

1-Octadecyl-3-Hexadecanesulfonyloxyazetidine

A. 1-octadecanoyl-3-hydroxyazetidine

Stir a suspension of 6.31 g of 3-hydroxyazetidine acetate in 150 ml dry pyridine until a solution results. Add 15.8 g stearoyl chloride at room temperature during ten minutes and stir for 21 hours at room temperature. Pour into 450 ml of an ice-water mixture, and extract once with 300 ml ethyl ether and then twice with 250 ml portions chloroform. Wash the combined extracts with three 150 ml portions of water, dry over anhydrous sodium sulfate and remove the solvents in vacuo. Stir the residue in 250 ml hexane and filter the resultant solid. Recrystallization from hexane affords pure 1-octadecanoyl-3-hydroxyazetidine, m.p. 86°–87.5° C.

B. 1-octadecyl-3-hydroxyazetidine

To a stirred solution of 85 ml of 0.98 M diborane in tetrahydrofuran, maintained at about 10° C. under a nitrogen atomsphere, add a solution of 8.16 g 1-octadecanoyl-3-hydroxyazetidine in 420 ml dry tetrahydrofuran over a period of 1.5 hours. Stir for one hour at room temperature then heat for 1.5 hours at 55°–60° C. Allow the reaction mixture to cool to room temperature and cautiously acidify with 30 ml 6 M aqueous hydrochloric acid. Reflux for one hour and distill in vacuo until about 150 ml solvent is removed. Dilute the residue with 450 ml water and basify with 20 ml 50% aqueous sodium hydroxide. Extract three times with 150 ml portions of ethyl ether, dry the combined ethereal extracts over anhydrous sodium sulfate, and strip off solvent in vacuo. Dissolve the residue in 150 ml ethanol containing 12 ml 1.9 M ethereal hydrochloric acid and reflux under nitrogen for 0.5 hour. Remove the solvent in vacuo and triturate the residue with 280 ml ethyl ether to obtain 1-octadecyl-3-hydroxyazetidine hydrochloride, m.p. 108.5°–115° C. Stir this hydrochloride salt with 120 ml water, 10 ml 2.5 M sodium hydroxide and 40 ml methylene chloride for one hour. Separate the layers and extract the aqueous layer three times with 100 ml portions of methylene chloride. Combine the organic layer and extracts, dry over anhydrous sodium sulfate and remove the solvents in vacuo to obtain 1-octadecyl-3-hydroxyazetidine, m.p. 75.5°–78° C.

C. 1-octadecyl-3-hexadecanesulfonyloxyazetidine

Rapidly add at room temperature a solution of 3.06 g hexadecanesulfonyl chloride in 16 ml dry benzene to a solution of 3.0 g 1-octadecyl-3-hydroxyazetidine and 1.67 g dicyclohexylamine in 250 ml dry benzene. Stir for about 20 hours at 35°–40° C. Concentrate the reaction mixture by removing solvent in vacuo, dilute with 250 ml ethyl ether, and filter the resultant precipitate. Treat the filtrate with a solution of 1.16 g maleic acid in 50 ml ethyl ether and filter the resultant solid. Recrystallization of this solid from ethyl acetate affords 3-hexadecanesulfonyloxyazetidine hemimaleate, m.p. 91°–97° C. Treatment of the hemimaleate salt with aqueous sodium hydroxide (as in the above step b) affords 1-octadecyl-3-hexadecanesulfonyloxyazetidine, m.p. 73.5°–75° C.

EXAMPLE 8

Ointment Formulation

| Ingredient | Amount |
| --- | --- |
| 1-isopropyl-3-methanesulfonyloxyazetidine hemimaleate, micronized | 0.05–20.0 mg |
| Mineral Oil, USP | 50.0 mg |
| White Petrolatum, USP to make | 1.0 g |

Procedure

A weighed quantity of white petrolatum and mineral oil are heated to 65° C. and uniformly mixed. The mixture is cooled to 50°–55° C. with stirring. The stated active ingredient which has been dispersed in a portion of the mineral oil and milled is added to the above with stirring. The ointment is cooled to room temperature.

EXAMPLE 9

Lotion formulation

| Ingredient | Amount |
| --- | --- |
| 1-Isopropyl-3-methanesulfonyloxyazetidine hemimaleate, micronized | 0.05–20.0 mg |
| Aluminum Monostearate | 50.0 mg |
| Isopropyl Myristate to make | 1.0 g |

Procedure

Heat about 90% of required isopropyl myristate to 60° C. Add aluminum monostearate with stirring and maintain heat to dissolve aluminum monostearate. Dissolve the stated active ingredient in the remaining quantity of isopropyl myristate. Add with stirring the solution of the stated active ingredient to the thickened solution of aluminum monostearate in isopropyl myristate previously cooled to 45° C. The lotion is cooled to room temperature with agitation.

EXAMPLE 10

Gel Formulation

| Ingredient | Amount |
| --- | --- |
| 1-Isopropyl-3-methanesulfonyloxyazetidine hemimaleate, micronized | 0.05–20.0 mg |
| Polyethylenes and Copolymers (A-C8) | 100.0 mg |
| Mineral Oil, Light to make | 1.0 g |

Procedure

Add a portion of mineral oil (about 90%) in a suitable vessel. Heat to about 80° C. Add polyethylene (A-C8) to the mineral oil. The mixture is agitated slowly while hot until all the polyethylene is dissolved. Cool the above mixture quickly by placing the vessel in a cooling bath of 10°–15° C. and resume the agitation. at normal speed. Once the content of the vessel reaches approximately 45° C., add a solution of the stated active ingredient which was dissolved in the remaining mineral oil at 45° C. to the above polymer solution. Allow the mixture to air cool with slow agitation. This will result in a gel form.

EXAMPLE 11

Ointment Formulation

| Ingredient | Amount |
| --- | --- |
| 3α-(3-methanesulfonyloxy-1-azetidinyl)-5α-cholestane hemimaleate, micronized | 1–20.0 mg |
| Mineral Oil, USP | 50.0 mg |
| White Petrolatum, USP   to make | 1.0 g |

Procedure

A weighed quantity of white petrolatum and mineral oil are heated to 65° C. and uniformly mixed. The mixture is cooled to 50°–55° C. with stirring. The stated active ingredient which has been dispersed in a portion of the mineral oil and milled is added to the above with stirring. The ointment is cooled to room temperature.

EXAMPLE 12

Lotion Formulation

| Ingredient | Amount |
| --- | --- |
| 3α-(3-methanesulfonyloxy-1-azetidinyl)-5α-cholestane hemimaleate, micronized | 1–50.0 mg |
| Aluminum Monostearate | 50.0 mg |
| Isopropyl Myristate   to make | 1.0 g |

Procedure

Heat about 90% of required isopropyl myristate to 60° C. Add aluminum monostearate. Dissolve the stated active ingredient in the remaining quantity of isopropyl myristate. Add with stirring the solution of the stated active ingredient to the thickened solution of aluminum monostearate in isopropyl myristate previously cooled to 45° C. The lotion is cooled to room temperature with agitation.

EXAMPLE 13

Gel Formulation

| Ingredient | Amount |
| --- | --- |
| 3α-(3-methanesulfonyloxy-1-azetidinyl)-5α-cholestane hemimaleate, micronized | 150.0 mg |
| Polyethylenes and Copolymers (A-C8) | 100.0 mg |
| Mineral Oil, Light   to make | 1.0 g |

Procedure

Add a portion of mineral oil (about 90% in a suitable vessel). Heat to about 80° C. Add polyethylene (A-C8) to the mineral oil. The mixture is agitated slowly while hot until all the polyethylene is dissolved. Cool the above mixture quickly by placing the vessel in a cooling bath of 10°–15° C. and resume the agitation at normal speed. Once the content of the vessel reaches approximately 45° C., add a solution of the stated active ingredient which was dissolved in the remaining mineral oil at 45° C. to the above polymer solution. Allow the mixture to air cool with slow agitation. This will result in a gel form.

What is claimed is:

1. A method of treating psoriasis which comprises administering to an individual in need of antipsoriatic therapy an antipsoriatic amount of a compound of the formula:

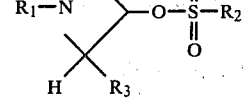

wherein $R_1$ is selected from the group consisting of hydrogen, alkyl groups containing 3–18 carbon atoms, cycloalkyl groups containing 5–15 carbon atoms, 1-adamantyl, 2-adamantyl, benzhydryl, benzyl, dihydroxybenzyl, dialkoxybenzyl, dibenzyloxybenzyl, and 3-(5α-cholestane) and 3-(5α-androstan-17-one) groups; $R_2$ is selected from the group consisting of alkyl groups containing 1–18 carbon atoms, benzyl and tolyl; and $R_3$ and $R_4$ are independently hydrogen or alkyl of 1–4 carbon atoms and the pharmaceutically acceptable acid addition salts thereof.

2. The method according to claim 1 wherein $R_1$ is an alkyl group containing from 3–18 carbon atoms.

3. The method according to claim 1 wherein $R_1$ is a 3-(5α-cholestane) group.

4. The method according to claim 2 wherein $R_1$ is an isopropyl group.

5. The method according to claim 2 wherein $R_2$ is an alkyl group containing from 1–18 carbon atoms.

6. The method according to claim 3 wherein $R_2$ is an alkyl group containing from 1–18 carbon atoms.

7. The method according to claim 3 wherein $R_2$ is a methyl group.

8. The method according to claim 5 wherein $R_2$ is a methyl group.

9. The method according to claim 1 wherein the compound is 1-isopropyl-3-methanesulfonyloxyazetidine hemimaleate.

10. The method according to claim 1 wherein the compound is 3α-(3-methanesulfonyloxy-1-azetidinyl)-5α-cholestane hemimaleate.

11. A topical pharmaceutical composition for the treatment of psoriasis comprising 0.05 to 5% by weight of a compound of the formula

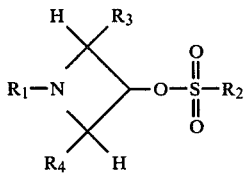

wherein $R_1$ is selected from the group consisting of hydrogen, alkyl groups containing 3–18 carbon atoms, cycloalkyl groups containing 5–15 carbon atoms, 1-adamantyl, 2-adamantyl, benzhydryl, benzyl, dihydroxybenzyl, dialkoxybenzyl, dibenzyloxybenzyl, and 3-(5α-cholestane) and 3-(5α-androstan-17-one) groups; $R_2$ is selected from the group consisting of alkyl groups containing 1–18 carbon atoms, benzyl and tolyl; and $R_3$ and $R_4$ are independently hydrogen or alkyl of 1–4 carbon atoms, and the pharmaceutically acceptable acid addition salts thereof in a vehicle suitable for topical administration.

12. A pharmaceutical composition according to claim 11 in the form of an ointment.

13. A pharmaceutical composition according to claim 11 in the form of a cream.

14. A pharmaceutical composition according to claim 11 which contains the compound 1-isopropyl-3-methanesulfonyloxyazetidine hemimaleate.

15. A pharmaceutical composition according to claim 11 which contains the compound 3α-(3-methanesulfonyloxy-1-azetidinyl)-5α-cholestane hemimaleate.

16. A compound of the formula:

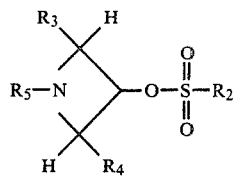

wherein $R_2$ is selected from the group consisting of alkyl containing 1-18 carbon atoms, benzyl and tolyl; $R_3$ and $R_4$ are independently hydrogen or alkyl of 1-4 carbon atoms; and $R_5$ is selected from the group consisting of 3-(5α-cholestane) and 3-(5α-androstan-17-one) groups and the pharmaceutically acceptable acid addition salts thereof.

17. A compound according to claim 16 wherein $R_2$ is a methyl group.

18. The compound according to claim 16 which is 3α-(3-methanesulfonyloxy-1-azetidinyl)-5α-cholestane hemimaleate.

* * * * *